(12) United States Patent
Klintenstedt et al.

(10) Patent No.: US 10,525,202 B2
(45) Date of Patent: Jan. 7, 2020

(54) CONTAINER HOLDER ASSEMBLY

(71) Applicant: SHL Group AB, Nacka Strand (SE)

(72) Inventors: Per Klintenstedt, Nacka (SE); Anders Wieselblad, Stockholm (SE); Gunnar Elmen, Huddinge (SE)

(73) Assignee: SHL MEDICAL AG, Zug (CH)

( * ) Notice: Subject to any disclaimer, the term of this patent is extended or adjusted under 35 U.S.C. 154(b) by 0 days.

(21) Appl. No.: 15/050,040

(22) Filed: Feb. 22, 2016

(65) Prior Publication Data
US 2016/0166769 A1 Jun. 16, 2016

Related U.S. Application Data

(63) Continuation of application No. 13/883,973, filed as application No. PCT/SE2011/051321 on Nov. 7, 2011, now Pat. No. 9,649,443.
(Continued)

(30) Foreign Application Priority Data

Nov. 8, 2010 (SE) ...................................... 1051160

(51) Int. Cl.
*A61M 5/31* (2006.01)
*A61M 5/24* (2006.01)
(Continued)

(52) U.S. Cl.
CPC .............. *A61M 5/3135* (2013.01); *A61J 1/16* (2013.01); *A61M 5/00* (2013.01); *A61M 5/24* (2013.01);
(Continued)

(58) Field of Classification Search
CPC ............ A61M 5/24; A61M 5/00; A61M 5/28; A61M 5/3142; A61M 5/3135;
(Continued)

(56) References Cited

U.S. PATENT DOCUMENTS 7,449,012 B2 * 11/2008 Young ................. A61M 5/2033
604/192
8,372,901 B2 2/2013 Hidrot et al.
(Continued)

FOREIGN PATENT DOCUMENTS

EP 0941133 B1 4/2004
EP 2021054 B1 3/2010
(Continued)

OTHER PUBLICATIONS

Sweden Patent Office, International Search Report issued in PCT/SE2011/051321, dated Feb. 22, 2012.
(Continued)

*Primary Examiner* — Jenna Zhang
(74) *Attorney, Agent, or Firm* — McDonnell Boehnen Hulbert & Berghoff LLP

(57) ABSTRACT

Container holder assembly for use in a medicament delivery device, comprising a tubular body elongated in an axial direction, said tubular body having a proximal end and an opposite distal end, and a retaining member releasably arranged to said tubular body for securing an elongated container placed inside the tubular body, wherein said retaining member comprises a resilient structure capable of exerting an axial force on said container in said tubular body for holding the container in a fixed position inside the tubular body and thereby avoiding displacement or breakage of the container and wherein a distal end of said container protrudes from a distal end of said tubular body.

25 Claims, 7 Drawing Sheets

Related U.S. Application Data

(60) Provisional application No. 61/411,020, filed on Nov. 8, 2010.

(51) Int. Cl.
*A61M 5/28* (2006.01)
*A61J 1/16* (2006.01)
*A61M 5/00* (2006.01)

(52) U.S. Cl.
CPC ....... *A61M 5/28* (2013.01); *A61M 2005/2407* (2013.01); *A61M 2005/2418* (2013.01); *A61M 2005/2433* (2013.01); *A61M 2005/2485* (2013.01); *A61M 2005/2488* (2013.01); *A61M 2005/3142* (2013.01)

(58) Field of Classification Search
CPC .. A61M 2005/2433; A61M 2005/2437; A61M 2005/244; A61M 2005/2418; A61M 2005/2477; A61M 2005/2481; A61M 2005/2485; A61J 1/16
See application file for complete search history.

(56) References Cited

U.S. PATENT DOCUMENTS

| | | | |
|---|---|---|---|
| 8,672,901 B2 | 3/2014 | Bollenbach et al. | |
| 8,992,487 B2 | 3/2015 | Eich et al. | |
| 9,649,443 B2* | 5/2017 | Klintenstedt | A61M 5/3135 |
| 9,861,753 B2* | 1/2018 | Klintenstedt | A61M 5/3135 |
| 2004/0236284 A1* | 11/2004 | Hoste | A61M 5/326 |
| | | | 604/198 |
| 2006/0030819 A1 | 2/2006 | Young et al. | |
| 2007/0021718 A1* | 1/2007 | Burren | A61M 5/24 |
| | | | 604/110 |
| 2010/0016793 A1* | 1/2010 | Jennings | A61M 5/2033 |
| | | | 604/134 |
| 2010/0152655 A1* | 6/2010 | Stamp | A61M 5/2033 |
| | | | 604/110 |
| 2010/0324496 A1* | 12/2010 | Plumptre | A61M 5/24 |
| | | | 604/207 |
| 2011/0169205 A1* | 7/2011 | Kempf | B29C 45/44 |
| | | | 267/180 |
| 2011/0306939 A1* | 12/2011 | Harms | A61M 5/24 |
| | | | 604/208 |
| 2012/0184917 A1* | 7/2012 | Bom | A61M 5/24 |
| | | | 604/187 |
| 2013/0204187 A1* | 8/2013 | Avery | A61M 5/24 |
| | | | 604/111 |
| 2013/0317452 A1* | 11/2013 | Heald | A61M 5/31545 |
| | | | 604/246 |
| 2014/0290792 A1* | 10/2014 | Avery | A61M 5/24 |
| | | | 141/18 |

FOREIGN PATENT DOCUMENTS

| | | |
|---|---|---|
| WO | 2009094793 A1 | 8/2009 |
| WO | 2009105909 A1 | 9/2009 |
| WO | 2010043533 A1 | 4/2010 |
| WO | 2010097116 A1 | 9/2010 |
| WO | 2010139635 A1 | 12/2010 |
| WO | 2012064258 A1 | 5/2012 |

OTHER PUBLICATIONS

Sweeden Patent Office, Written Opinion issued in PCT/SE2011/051321, dated Feb. 22, 2012.

* cited by examiner

CONTAINER HOLDER ASSEMBLY

CROSS REFERENCE TO RELATED APPLICATIONS

The present application is a continuation application of U.S. patent application Ser. No. 13/883,973 filed May 7, 2013, which is a 371 of International Patent Application No. PCT/SE2011/051321, filed Nov. 7, 2011 which claims the benefit of U.S. Provisional Patent Application No. 61/411,020, filed Nov. 8, 2010 the entire contents of which are incorporated entirely herein by reference.

TECHNICAL FIELD

The present invention relates to a cartridge assembly for medicament delivery devices and in particular to a cartridge assembly where safety and handling aspects have been improved by the interaction of a cartridge, a cartridge holder and a cartridge retainer.

BACKGROUND

A medicament delivery device, such as an injector, is often arranged with a container holder to allow operations to be carried out on the container, for instance displacement within the injector housing during skin penetration, expulsion of medicament by a plunger acting on the stopper in the container, penetration of the septum using a needle and replacement of container. Because of tolerances, manufactured containers vary in size, which may result in the position of the container within the holder being somewhat affected during handling of the device. For instance, displacement of the container may occur as a result of penetrating the septum of the container with a needle or by sudden impact forces to the housing of the device. If the container is not exactly positioned in relation to the holder, the stroke length of the plunger rod—and consequently the dosage set by the user or the manufacturer of the device—will not be exactly correlated to the actual position of the container, resulting in the wrong dose being delivered. Also, movement of the container within the holder may lead to a higher risk of breaking the container due to impact forces between the holder and the container.

A number of prior art solutions to container holders are known:

US 2007/0021718 A1 describes a spring for use as a supporting device between a container and a housing in order to firmly position the container within the housing. The spring is not attached to the container holder but wedged between an insert and the container, or attached to the housing of a power pack. Therefore it is not suited to secure the container to the container holder on its own.

EP 0 941 133 B1 discloses a cartridge assembly intended to key a cartridge to a certain type of injection pen in order to prevent cross-use of different cartridges and pens, which could result in the wrong drug being used or the patient receiving the wrong dose. Various embodiments describe a cartridge assembly where the cartridge is secured in a cartridge holder that is adapted for a specific cartridge and for a specific pen. Also, the rigid construction using cooperating threaded holder parts to secure the cartridge could lead to damage to the cartridge if too much force is used to join the parts.

WO 2010/097116 A1 describes a container holder for securely holding a container wherein the holder includes a support for the shoulder of the container in the front end, flexible arms exert a compressive radial force on the sides of the container and hooks at the rear end keep the container inside the container once it has been inserted in the container holder and pushed past the hooks. There is no resilient member that holds the container in the same position in relation to the holder, i.e. due to tolerances the container may be slightly axially displaced during handling of the device.

US 2006/0030819 A1 discloses a cartridge container arranged with inwardly directed resilient tabs that apply a radial compressive force on the cartridge to align and to hold it in proper orientation and to hinder axial and radial movement of the cartridge inside the cartridge container during loading. The use of resilient tabs allows accommodation of cartridges of different sizes, but no compressive force is used to bias the cartridge axially.

EP 2 021 054 B1 describes an injection device wherein a syringe may be moved from a retracted position to an extended position for discharging its contents and wherein the syringe is held by a syringe carrier. The syringe is held in the carrier by arms arranged with lugs and dampers that grip the rear surface of a flange of the syringe in order to minimize the risk of the syringe breaking by impact force such as caused by sudden movement, i.e. during extension or retraction of the syringe. No precaution is taken to fix the syringe in a predetermined position inside the carrier.

Therefore, there is a need for a device that can securely keep the container in one predetermined position in relation to the container holder in order to be able to deliver a set dose in a safe and reliable way without damaging the holder. With regard to cost and complexity the device needs to be easy to manufacture and to implement in existing devices. The resulting device must also be simple and intuitive for the end user to operate.

SUMMARY

According to the main aspect of the invention, it relates to a container holder assembly for use in a medicament delivery device, comprising a tubular body elongated in an axial direction, said tubular body having a proximal end and an opposite distal end, and a retaining member releasably arranged to said tubular body for securing an elongated container placed inside the tubular body, said retaining member comprises a resilient structure capable of exerting an axial force on said container in said tubular body for holding the container in a fixed position inside the tubular body and thereby avoiding breakage or displacement of the container wherein a distal end of said container protrudes from a distal end of said tubular body.

According to another aspect of the invention the container comprises a shoulder portion abutting a proximal inner annular ledge of the tubular body.

According to a further aspect of the invention the retaining member further comprises an annular housing arranged to accommodate a resilient structure.

According to yet another aspect of the invention said retaining member is capable of accommodating said tubular body such that a distal surface of an annular spacer abuts a circumferential flange of the tubular body.

According to yet a further aspect of the invention said retaining member is adapted to be releasably attached to a proximal end of a delivery device such that the distal end of said container is resiliently pressed against a stopping element of said delivery device.

According to another aspect of the invention the resilient structure comprises at least one resilient washer and an annular spacer.

According to a final aspect of the invention the container holder assembly is to be used in a medicament delivery device.

There are a number of advantages with the present invention. The use of a resilient structure in a retaining member allows a container to be fixed within a holder, regardless of size differences of different containers, such as arising from tolerances, since the resilient structure adapts its size to the size of the container. The container may otherwise be accidentally displaced during handling and during attachment of a delivery member. When the container is fixed within the holder the stroke length of a plunger of a delivery device may be accurately determined so that precise doses can be delivered.

Another advantage of the structure of the retaining member is the resiliency that permits a softer tensioning of the grip on the container as compared to the grip exerted by a rigid retainer. This helps to prevent damage to the container caused by careless tensioning of the container holder/retainer. It also protects the container from otherwise damaging impacts that may occur during handling of the device.

Yet another advantage of a retainer is that it prevents the container from accidentally falling out of the container holder during handling before it is attached to a delivery device. It is also relatively protected within the container holder as compared to outside the holder.

Also, since the assembly is delivered to the user in a semi-assembled state it is easy for the user to insert a container and arrange the container holder assembly to a delivery device to administer medicament.

These and other aspects and advantages of the present invention will become apparent from the following detailed description and from the accompanying drawings.

BRIEF DESCRIPTION OF THE DRAWINGS

In the following description of embodiments of the invention, reference will be made to the accompanying drawings of which.

DETAILED DESCRIPTION

Embodiments of the present invention will now be described in detail. As should be noted in the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

According to a main aspect of the invention it relates to a container holder assembly for use in a medicament delivery device, which container holder assembly comprises a tubular body elongated in an axial direction, said tubular body having a proximal end and an opposite distal end A retaining member is releasably arranged to said tubular body for securing an elongated container placed inside the tubular body. The retaining member comprises a resilient structure that is capable of exerting an axial force on said container in said tubular body for holding the container in a fixed position inside the tubular body and thereby avoiding breakage or displacement of the container.

Figure 1:
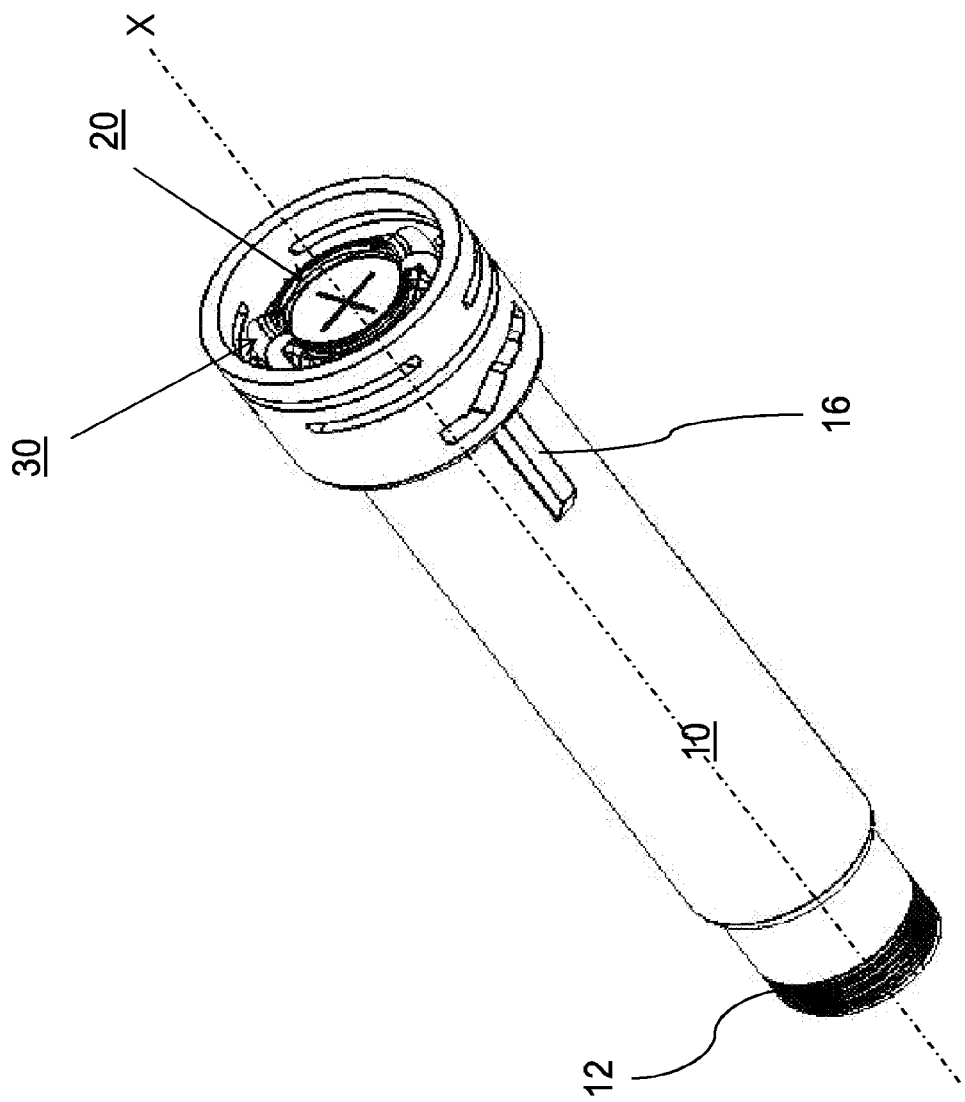
FIG. 1 is a perspective view of a first embodiment of the present invention in an assembled position.

An exemplary embodiment of the present invention is shown in the FIGS. 1-4. The embodiment shown in the figures is a container holder assembly for medicament delivery devices but is not restricted to it. FIG. 1 is a perspective view of exemplary components of such a container holder assembly. A tubular body 10, such as a container holder, is elongated along an axis X with a closed proximal end and an open distal end for receiving a container 20. In order to secure the container 20 inside the tubular body 10, a retaining member 30 is arranged to the container holder for gripping the container and resiliently urging it into abutment with a stop surface inside the tubular body 20.

The exemplary embodiment disclosed in FIG. 1 shows the retaining member 30 arranged at the open, distal end of the tubular body 10, gripping the distal end of the container 20. The invention is not restricted to this arrangement however. The container holder assembly may be may be constructed in many different ways without departing from the concept of the present invention. The resilient structure of the retaining member 30 will be explained below.

The tubular body 10 may also be arranged with radially protruding elements 16 arranged to key the container holder assembly to a certain type of delivery device in order to prevent the use of the assembly in a device that it is not intended for.

A proximal part of the tubular body 10 may be arranged with an interface 12, such as threads, for connecting a delivery member (not shown). The delivery member may be a needle, a nozzle, a mouth piece, or the like.

Figure 2:
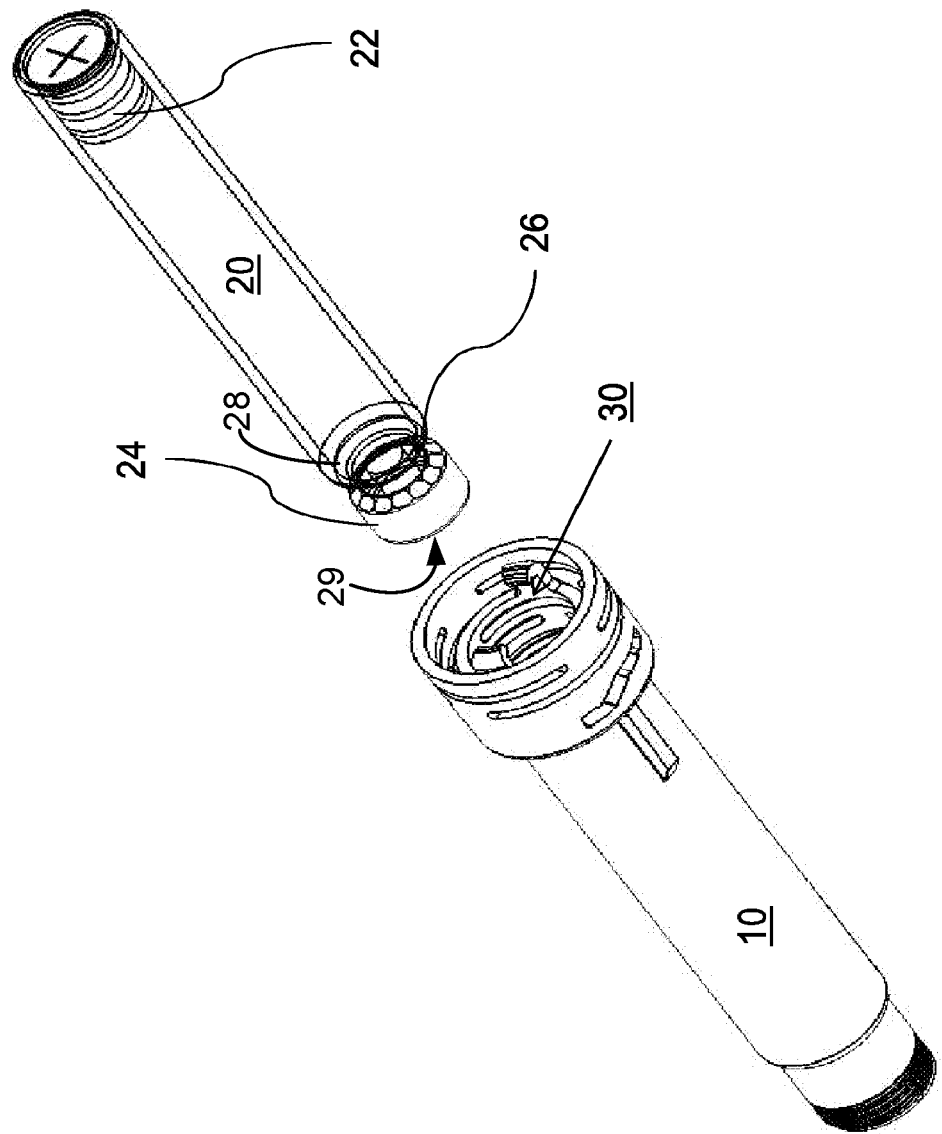
FIG. 2 is a perspective view of a first embodiment of the present invention showing a container outside the container holder assembly.

FIG. 2 shows the assembly in a semi-assembled state, wherein the container 20 has not yet been loaded in the tubular body 10 and wherein the retaining member 30 is loosely arranged to the tubular body 10, prepared for receiving the container 20. The physical dimensions of the assembly are adapted to a certain type of container but the present invention allows for large dimensional tolerances of the containers thanks to the resilient structure of the retaining member 30, which holds the container in a predetermined position inside the container holder despite variations in physical dimensions of the container.

Figure 6:
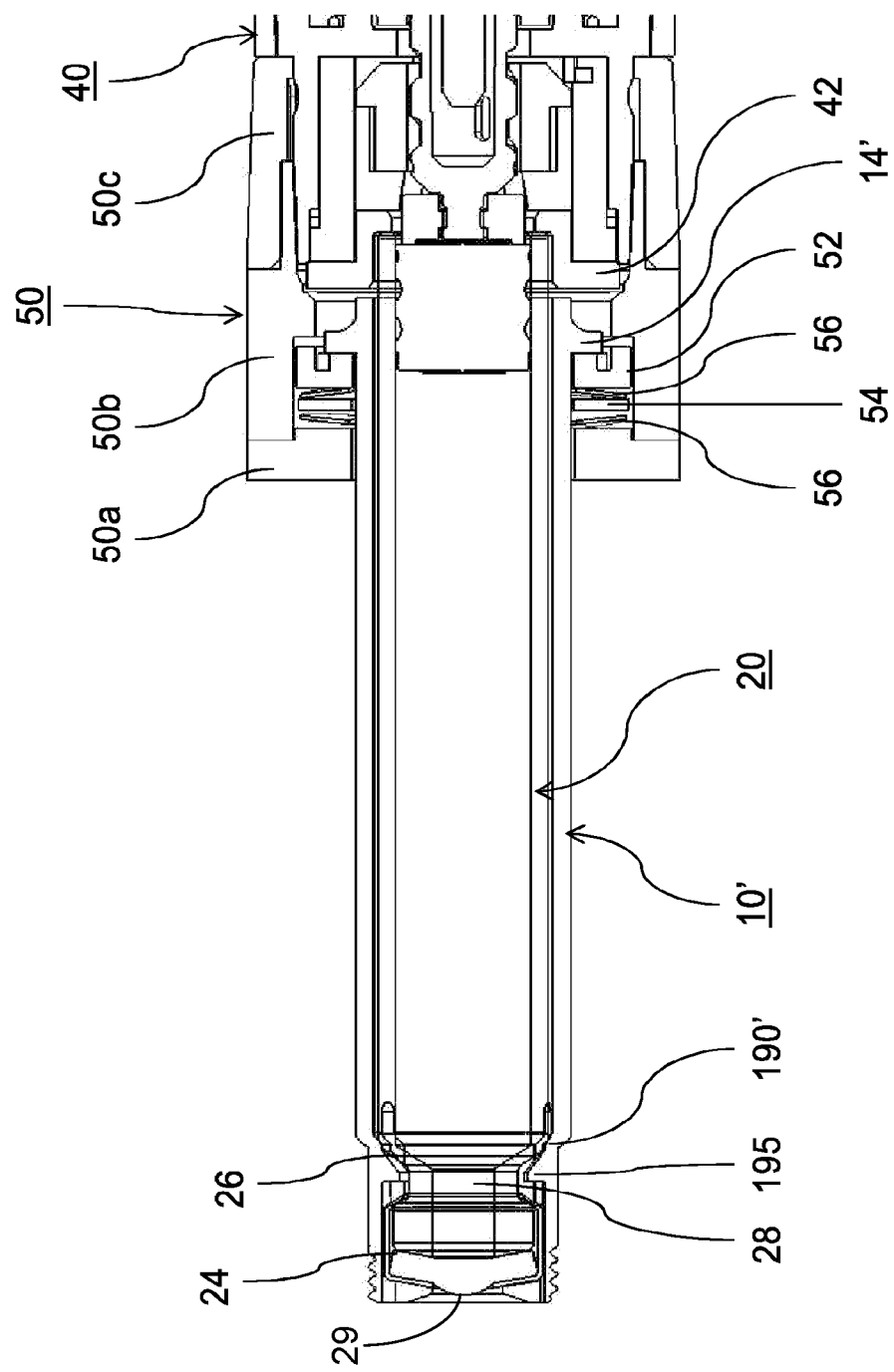
FIG. 6 is a cross-sectional view of a second embodiment of the invention.

An exemplary container 20, as show in FIGS. 2 and 6, may contain medicament and is tubular and made of glass. A proximal end typically has a shoulder portion 26 connecting the tubular part with a neck portion 28 and a cap 24. The cap comprises a septum 29 (see FIG. 6) that seals the proximal end of the container. The distal end of the container is sealed by an axially movable stopper 22.

Figure 3:
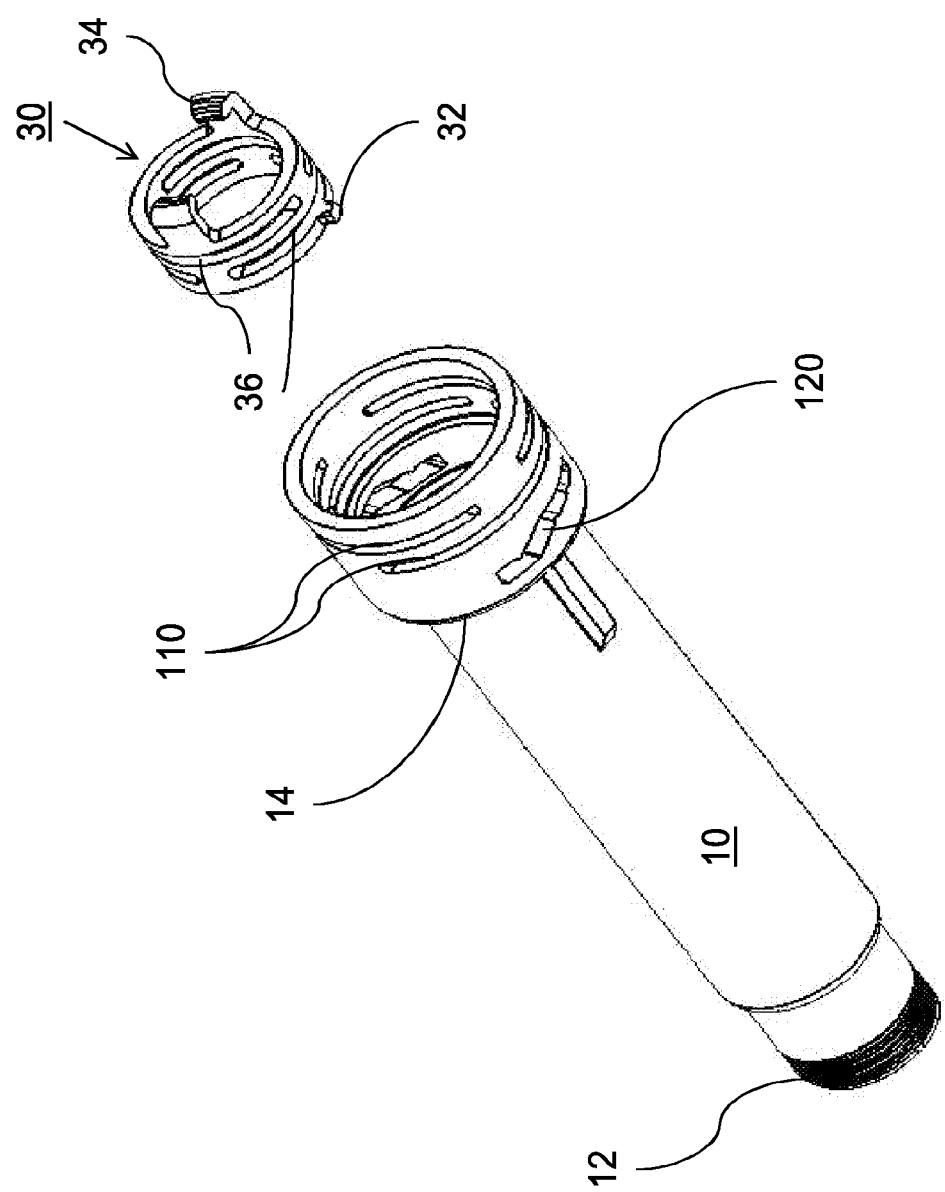
FIG. 3 is a perspective view of a first embodiment of the present invention showing the container holder assembly in a disassembled position.

FIG. 3 depicts an embodiment of the invention. The retaining member 30, which is here shown outside the tubular body 10, comprises a resilient structure that allows the body of the retaining member to be flexible in the axial direction, i.e. to stretch or to compress, so that the proximal end and the distal end of the retaining member may be axially displaced with regard to each other. The resilient structure 36 is achieved by forming circumferentially elongated cut-outs, or slits, in the tubular wall of the retaining member 30. The slits are arranged in at least two parallel circumferentially aligned rows, wherein a space between any two slits of one row is aligned with the centre of a slit of an adjacent row.

At least two gripping means 34 are arranged on the distal annular end surface of the retaining member 30. The gripping means 34 may be formed as distally protruding, inwardly curved hooks that are able to flex radially outwards as the container 20 is pushed inside the tubular body 10. Each gripping means is aligned with the centre of one of the most distal slits.

The proximal portion of the retaining member 30 is arranged with a first locking means 32 capable of mutual mechanical connection with a second locking means 120 of the tubular body 10. The first locking means 32 may be formed as at least two protrusions, or guide knobs, that extend radially outwardly from the outer circumferential surface of the retaining member 30, whereas the second locking means 120 may be formed as a cut-out, or guide track, that is able to guide a protrusion of the first locking means 32 along the track as the first and second locking means are axially rotated in relation to each other, i.e. in the fashion of a bayonet connection. Each protrusion is aligned with the centre of one of the most proximal slits.

The gripping means 34 are arranged to abut the distal annual end surface of the container 20 when the container has been placed in the tubular body 10 and the first and second locking means are brought into locking position with each other (explained in detail below).

The resiliency of the retaining member 30 of the exemplary embodiment of FIG. 3 results from the careful alignment of the slits, the gripping means 34 and the first locking means 32. For best performance, the number of gripping means equals the number of slits in the most distal row of slits and the number of first locking means equals the number of slits in the most proximal row of slits. Preferably, the number of slits in one row equals the number of slits in each of the other rows. Most preferably, the number of slits in one row equals two. To achieve good resiliency it is also preferable that the circumferential length occupied by a slit is significantly larger than the circumferential length occupied by the space between two slits of any adjacent rows.

Figure 4:
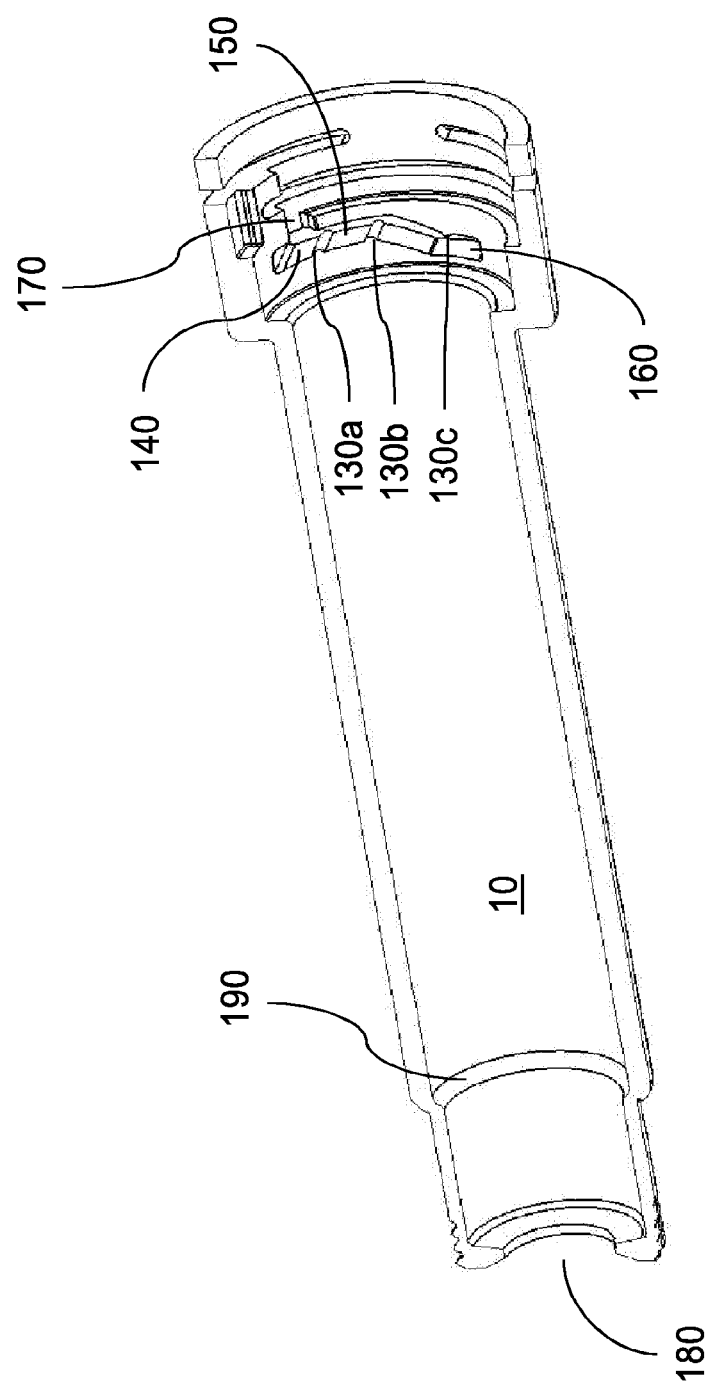
FIG. 4 is a cross-sectional view of a first embodiment of the present invention showing the inside of the container holder.

In a similar fashion, an end—preferably the distal end—of the tubular body 10 may be arranged with a second resilient structure 110. As the container holder assembly, with a container inside, is inserted by a user in a delivery device by attaching the tubular body to holding means (not shown) arranged at a proximal receiving end of the device (not shown). The distal annular end surface of the tubular body thereby comes into abutment with a surface of the delivery device, forcing the second resilient structure 110 to compress axially. The user may then attach a delivery member to the interface 12 in order to use the device FIG. 4 shows a cross-section of the exemplary embodiment of the tubular body 10. The second locking means 120 (FIG. 2) may be formed as a cut-out, or guide track, that is able to guide a protrusion of the first locking means 32 along the track as the first and second locking means are axially rotated in relation to each other. The track has a distally directed opening 170 through which the first locking means 32 of the retaining member 30 may be inserted into the track. After insertion the first locking means is in the initial position 140 of the second locking means. By slightly rotating the tubular body 10 and the retaining member 30 with respect to each other, for instance by using a specialized tool, the first locking means is forced past a first stopper 130a arranged to prevent unintentional rotation of the locking means. The first locking means is then in a loading position 150, as depicted in FIG. 2. In the loading position 150 the container holder assembly is ready for insertion of a container 20 into the tubular body 10. As the container is pushed into the tubular body the gripping means 34 flex radially outwards, snapping back as the distal end of the container passes the gripping means. The container is now loosely secured in the tubular body, resting with its shoulder portion 26 against the inner annular ledge 190 of the tubular body 10. The container will not fall out since the gripping means 34 is blocking movement in the distal direction and the first locking means 32 is confined between the first stopper 130a and a second stopper 130b. However, in the loading position, the retaining member still does not exert an axial force on the container.

To achieve the object of the invention, i.e. to fix the container in an exact predetermined position in the tubular body 10, an axial force needs to be exerted between the tubular body and the container, such that they are pressed towards each other. In the exemplary embodiment of FIG. 4 this is attained by further rotation of the retaining member with regard to the tubular body. When the first locking means 32 is forced past the second stopper 130b the track of the second locking means deviates from a circumferential path to a circumferential/axial path, forcing the proximal part, i.e. the first locking means and consequently the whole the retaining member in a proximal, axial direction. Since the gripping means 34 is arranged to abut the distal annular surface of the container 20 and the container is hindered from proximal displacement because it is resting with its shoulder portion 26 in abutment with the inner annular ledge 190 of the tubular body 10, the resilient structure 36 begins to stretch axially in the proximal direction. The tensioned resilient structure exerts an axial force such that the gripping means 34 urges the shoulder portion 26 of the container 20 and the inner annular ledge 190 of the tubular body 10 against each other.

As the retaining member and the tubular body are further rotated with regard to each other, the track of the second locking means 120 eventually returns to a circumferentially aligned path. The first locking means is forced past the third stopper 130c and comes to rest in a holding position 160, abutting the distal surface of the track due to the axial force exerted by the resilient structure 36.

The overall pitch of the track of the second locking means is carefully determined during manufacture of the assembly to achieve a force that is strong enough to fix the container inside the tubular body, regardless of the tolerances of the container used, but at the same time to achieve a force that is not so strong as to risk damaging the container.

Another parameter that may be used to calibrate the force during manufacturing is the resiliency of the resilient structure 36. This may be varied, for instance by selecting an appropriate number of rows of slits of the resilient structure, or by the material chosen for the container holder assembly, or by the thickness of the wall of the retaining member or the distance between the rows of slits, etc.

Other designs of the locking means 32, 120 are also conceivable, such as mutually engaging threads.

Figure 5:
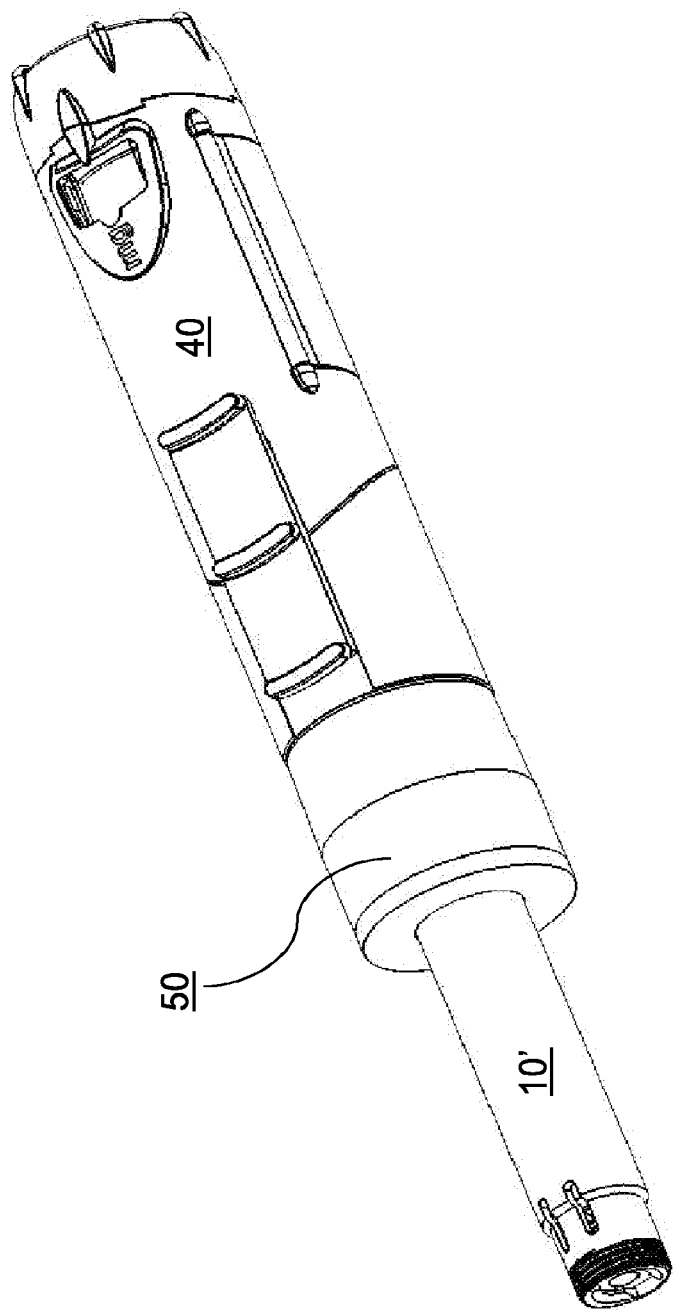
FIG. 5 is a perspective view of a second embodiment of the invention.
Figure 7:
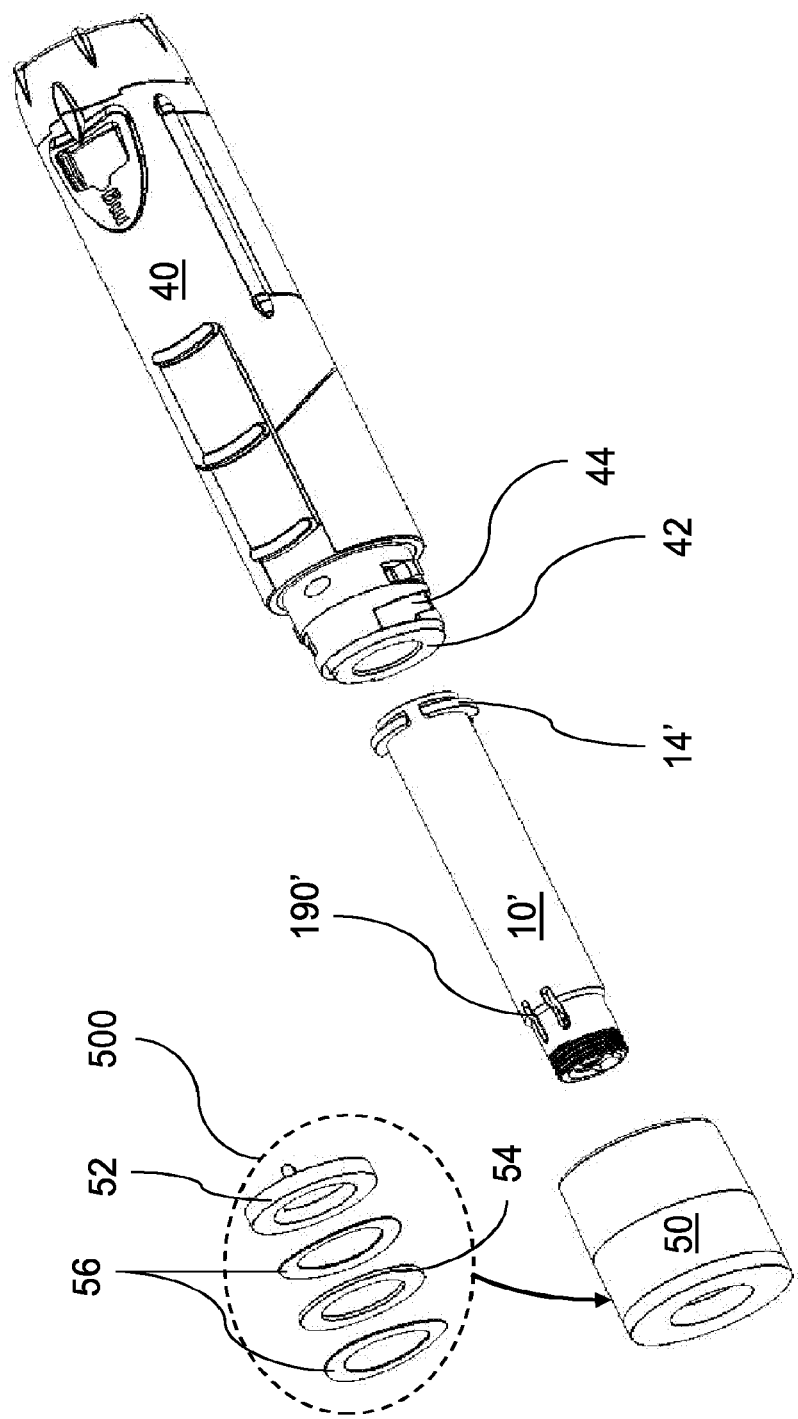
FIG. 7 is an exploded perspective view of a second embodiment of the invention.

A second exemplary embodiment of the present invention is shown in FIGS. 5-7. FIG. 5 is a perspective view of a medicament delivery device 40 to which a container holder 10', comprising a container (not shown), has been attached using retaining member 50.

FIG. 6 shows a cross-section of the connection between the device 40 and the container holder 10' of FIG. 5. The retaining member 50 is, in the exemplary embodiment shown, comprised of a first part 50a, a second part 50b and a third part 50c that together form an axially aligned annular housing with a through-going axially aligned hole for accommodating the container holder 10' with the container 20. The retaining member 50 also houses a resilient structure 500 comprising at least one resilient washer 56, and a spacer 56. If multiple resilient washers are used, at least one supporting washer 54 is positioned between them in order to separate the resilient washers from each other.

The third part 50c of the retaining member comprises attachment means (not shown) on a distal circumferential surface for mutually connecting with engagement means 44 on a proximal circumferential surface of the delivery device 40. Various solutions are conceivable for the mutual connection of the retaining member and the delivery device, e.g. such as a threaded connection or bayonet connection.

The retaining member 50 and its constituent components are assembled during manufacturing and are designed for a predetermined kind of container holder 10', which in turn is designed to hold a predetermined kind of container 20. The object of the invention, however, is to allow large tolerances in the physical dimensions of the container 20 without affecting the accuracy of the dose delivery, i.e. by holding the container in a fixed position in relation to the container holder, and without damaging the container. This is achieved by resilient fixation of the container in the holder.

The function of the retaining member 50 will now be described in conjunction with FIG. 7, which is an exploded view of the delivery device 40 and the container holder assembly, i.e. the retaining member 50 and the container holder 10'. Also shown is an inserted exploded image of the resilient structure 500 housed in the resilient means 50.

The resiliency of the retaining member 50 is a function of the stack of resilient washers 56. The washers may, for instance, have a wavy shape that results in an axial restoring force if the washers are compressed. Since the shape of the individual resilient washers is identical a supporting washer 54 may be used to separate them from each other. Otherwise, adjacently packed resilient washers would result in much reduced flexibility.

When the delivery device is to be used a container is inserted in the tubular body 10' by the distal end. At least two radially inwardly protruding cut-outs in the form of flexible tongues 195 are arranged in the circumferential wall of the tubular body 10' to flex radially outwards as the cap 24 is pushed against the tongues in order to let the container pass. Thereafter, the tongues flex back inwards, preventing return-movement of the container and securing it by its neck portion 28 (FIG. 6) inside the tubular body 10' such that it cannot accidentally fall out before the container holder assembly has been attached to the delivery device 40. When the container is secured in the tubular body, the distal end of the container still protrudes distally of the tubular body, the function of which will be explained below.

The tubular body 10' holding the container is then inserted in the retaining member 50 from the distal side such that the proximal surface of the circumferential flange 14' arranged at the distal end of the tubular body comes to rest against the distal surface of the annular spacer 52. The container holder assembly, including the container, is subsequently attached to the proximal end of the delivery device by the mutual connection described above.

As the mutual connection of the container holder assembly and the delivery device is tightened, such as by turning the retaining member 50 in relation to the delivery device 40 for mutually engaging threads or for operating a bayonet connection, the protruding distal annular surface of the container abuts the stopping element 42. The abutting function of the stopping element could also be achieved by an integrated surface of the delivery member 40 itself, such as a surface of the housing.

Further tightening of the connection results in compression of the resilient washers 56 between the first part 50a and the spacer 52 resting against the flange 14'. This leads to a restoring axial force, arising from the compressed resilient washers 56, that acts on the flange 14' to urge the tubular body 10' in the distal direction. Since the container 20 abuts the stopping element 42, the inner annular ledge 190' is brought into abutment with the shoulder portion 26 of the container, forcing the container against the stopping element 42. The force arising from the compression of the resilient washers 56 thereby fixes the container with regard to the tubular body 10' and the delivery device 40.

The present invention is not limited to the above-described preferred embodiments. Various alternatives, modifications and equivalents may be used. Therefore, the above embodiment should not be taken as limiting the scope of the invention, which is defined by the appended claims.

The invention claimed is:

1. A container holder that releasably attaches to a medical delivery device, the container holder comprising:
   a tubular body elongated in an axial direction and configured for releasable attachment to a proximal end of the medical delivery device, the tubular body comprising a proximal end and a distal end defining a resilient portion, wherein the resilient portion is monolithic,
   wherein the resilient portion of the distal end of the tubular body comprises a distally-facing, annular opening configured to receive a container through the opening;
   wherein the resilient portion of the distal end of the tubular body is configured to compress axially along a longitudinal direction when a distal annular end surface of the resilient portion of the distal end of the tubular body comes into abutment with a surface of the medical delivery device during attachment of the tubular body to the proximal end of the delivery device; and
   wherein the resilient portion of the distal end of the tubular body is attached to an outer circumferential surface of the distal end of the tubular body.

2. The container holder of claim 1,
   wherein the resilient portion comprises a locking mechanism that mechanically connects with a flexible retaining member for securing the container placed inside the tubular body.

3. The container holder of claim 2,
   wherein the locking mechanism of the tubular body comprises a cut-out.

4. The container holder of claim 3,
   wherein the locking mechanism of the tubular body is able to guide at least one protrusion of the flexible retaining member along the cut-out,
   as the locking mechanism and the flexible retaining member are axially rotated in relation to one another.

5. The container holder of claim 3,
   wherein the cut-out comprises a circumferential path.

6. The container holder of claim 3,
wherein the cut-out comprises an axial path.

7. The container holder of claim 2,
wherein the locking mechanism of the tubular body comprises a guide track.

8. The container holder of claim 7,
wherein the locking mechanism of the tubular body is able to guide at least one protrusion of the flexible retaining member along the guide track
as the locking mechanism and the flexible retaining member are axially rotated in relation to one another.

9. The container holder of claim 8,
wherein the locking mechanism further comprises a distally directed opening through which the flexible retaining member may be inserted into the guide track.

10. The container holder of claim 9,
wherein after insertion of the flexible retaining member into the distally directed opening of the locking mechanism,
rotation of the tubular body with respect to the flexible retaining member forces the flexible retaining member past a stopper arranged to prevent unintentional rotation of the locking mechanism.

11. The container holder of claim 7,
wherein the guide track comprises a circumferential path.

12. The container holder of claim 7,
wherein the guide track comprises an axial path.

13. The container holder of claim 2,
wherein the locking mechanism of the tubular body comprises a resilient structure.

14. The container holder of claim 2, wherein the distal end of the tubular body comprises a distal annular end surface,
wherein, when the tubular body is releasably attached to the delivery device, the distal annular end surface of the tubular body comes into abutment with the surface of the delivery device, forcing the locking mechanism to compress.

15. The container holder of claim 1, wherein the tubular body comprises an elongated tubular body, the elongated tubular body comprising a closed proximal end and an open distal end for receiving the container.

16. The container holder of claim 15, wherein the container comprises a shoulder portion abutting a proximal inner annular ledge of the elongated tubular body.

17. The container holder of claim 1,
wherein the tubular body comprises a plurality of radially inwardly protruding cut outs arranged on a circumferential wall of the tubular body.

18. The container holder of claim 17,
wherein the plurality of radially inwardly protruding cut outs comprise flexible tongues.

19. The container holder of claim 1,
wherein the tubular body further comprises at least one radially protruding element arranged to key the container holder to only a certain type of delivery device in order to prevent the use of the container holder with a delivery device that the container holder is not intended for.

20. The container holder of claim 1,
wherein the tubular body further comprises an interface for connecting a delivery member to the tubular body.

21. The container holder of claim 20,
wherein the interface comprises threads for connecting the delivery member to the tubular body.

22. The container holder of claim 20,
wherein the interface comprises a bayonet connection for connecting the delivery member to the tubular body.

23. The container holder of claim 1,
wherein the container holder holds a container,
wherein the container comprises a proximal end comprising a shoulder portion connecting a tubular part with a neck portion and a cap,
the cap comprising a septum that seals the proximal end of the container.

24. The container holder of claim 23,
wherein the container further comprises a stopper that seals a distal end of the container.

25. The container holder of claim 1,
wherein the resilient portion comprises at least one circumferentially elongated cut out cut-out in a tubular wall.

* * * * *